(12) United States Patent
Sun et al.

(10) Patent No.: US 11,915,446 B2
(45) Date of Patent: Feb. 27, 2024

(54) GENERATING A MEDICAL RESULT IMAGE

(71) Applicant: Siemens Healthcare GmbH, Erlangen (DE)

(72) Inventors: Qi Sun, Beijing (CN); Jing Feng Han, Shanghai (CN)

(73) Assignee: SIEMENS HEALTHINEERS AG, Erlangen. (DE)

( * ) Notice: Subject to any disclaimer, the term of this patent is extended or adjusted under 35 U.S.C. 154(b) by 443 days.

(21) Appl. No.: 17/284,872

(22) PCT Filed: Oct. 24, 2018

(86) PCT No.: PCT/CN2018/111674
§ 371 (c)(1),
(2) Date: Apr. 13, 2021

(87) PCT Pub. No.: WO2020/082268
PCT Pub. Date: Apr. 30, 2020

(65) Prior Publication Data
US 2021/0358168 A1 Nov. 18, 2021

(51) Int. Cl.
*G06T 7/73* (2017.01)
*G06T 7/11* (2017.01)
(Continued)

(52) U.S. Cl.
CPC .................. *G06T 7/74* (2017.01); *G06T 7/11* (2017.01); *G06T 7/174* (2017.01); *G06T 7/37* (2017.01);
(Continued)

(58) Field of Classification Search
CPC ... G06T 7/74; G06T 7/11; G06T 7/174; G06T 7/37; G06T 2207/10081;
(Continued)

(56) References Cited

U.S. PATENT DOCUMENTS 8,768,101 B1 * 7/2014 Repperger ............ G06V 10/242
382/296
9,325,861 B1 * 4/2016 Ettinger ............. H04N 1/00183
(Continued)

FOREIGN PATENT DOCUMENTS

CN 1910616 A 2/2007
CN 101005803 A 7/2007
(Continued)

OTHER PUBLICATIONS

Baert, S.A.M. et al.: "Guide wire tracking during endovascular interventions"; in IEEE Trans. Med. Imaging; vol. 28, No. 8; pp. 965-972; 2003.
(Continued)

*Primary Examiner* — Dominic E Rego
(74) *Attorney, Agent, or Firm* — Harness, Dickey & Pierce, P.L.C.

(57) ABSTRACT

A method is for generating a medical result image using a current image, a target image and a reference image. All images depict at least partially the same body region of a patient. In an embodiment, the method includes defining at least one image segment within the target image; registering the reference image with the target image by establishing a registration matrix for each image segment within the target image, the respective registration matrix being specific for the respective image segment; detecting a position of a surgical instrument in the current image, the position corresponding to an image segment of the target image; and generating the medical result image by fusing the current image and the reference image using the registration matrix assigned to the image segment according to the position of the surgical instrument within the current image.

20 Claims, 3 Drawing Sheets

(51) Int. Cl.
*G06T 7/174* (2017.01)
*G06T 7/37* (2017.01)

(52) U.S. Cl.
CPC ............... *G06T 2207/10081* (2013.01); *G06T 2207/10088* (2013.01); *G06T 2207/20221* (2013.01); *G06T 2207/30021* (2013.01)

(58) Field of Classification Search
CPC . G06T 2207/10088; G06T 2207/20221; G06T 2207/30021
See application file for complete search history.

(56) References Cited

U.S. PATENT DOCUMENTS

| | | | |
|---|---|---|---|
| 2005/0004454 A1 | 1/2005 | Mitschke et al. | |
| 2005/0027187 A1 | 2/2005 | Barth et al. | |
| 2005/0203385 A1 | 9/2005 | Sundar et al. | |
| 2005/0232356 A1* | 10/2005 | Gomi | H04N 19/51 375/E7.123 |
| 2006/0291707 A1* | 12/2006 | Kothapalli | G06T 7/0012 382/280 |
| 2008/0221435 A1 | 9/2008 | Rasche | |
| 2008/0304615 A1 | 12/2008 | Mielekamp | |
| 2009/0087124 A1* | 4/2009 | Nord | G06V 10/754 382/296 |
| 2009/0226060 A1 | 9/2009 | Gering et al. | |
| 2010/0073502 A1* | 3/2010 | An | G06T 7/248 348/222.1 |
| 2010/0239125 A1* | 9/2010 | Chang | G06V 10/751 382/103 |
| 2012/0321195 A1* | 12/2012 | Jhunjhunwala | G06T 7/33 382/195 |
| 2013/0053679 A1 | 2/2013 | Owen | |
| 2014/0336509 A1* | 11/2014 | Kang | A61B 8/5246 600/443 |
| 2015/0100406 A1* | 4/2015 | Klimetschek | G06Q 30/0242 705/14.41 |
| 2016/0171657 A1* | 6/2016 | Matson | G06T 5/003 382/299 |
| 2016/0249984 A1 | 9/2016 | Janssen | |
| 2017/0278229 A1* | 9/2017 | Zhu | G06T 5/003 |
| 2017/0372474 A1 | 12/2017 | Behar et al. | |
| 2018/0168732 A1 | 6/2018 | Trousset et al. | |
| 2019/0108622 A1* | 4/2019 | Douady-Pleven | H04N 23/741 |
| 2019/0154410 A1* | 5/2019 | Nelson | G02C 7/104 |
| 2020/0244862 A1* | 7/2020 | Wang | H04N 23/667 |
| 2022/0256076 A1* | 8/2022 | Douady | H04N 19/597 |

FOREIGN PATENT DOCUMENTS

| | | |
|---|---|---|
| CN | 101237813 A | 8/2008 |
| CN | 101283910 A | 10/2008 |
| CN | 101969852 A | 2/2011 |
| CN | 103353992 A | 10/2013 |
| CN | 104812307 A | 7/2015 |
| CN | 107545585 A | 1/2018 |

OTHER PUBLICATIONS

Wang, Peng et al.: "Robust Guidewire Tracking in Fluoroscopy"; in: Proc. IEEE Comput. Vis. Pattern Recognit; pp. 691-698; 2009.

Lessard, Simon et al. "Automatic detection of selective arterial devices for advanced visualization during abdominal aortic aneurysm endovascular repair" Medical Engineering and Physics, vol. 37 No. 10, pp. 979-986, 2015 http://dx.doi.org/10.1016/j.medengphy.2015.07.007.

Zhang, Qiang et al.: "Three-dimensional image fusion of CTA and angiography for real-time guidance during neurointerventional procedures"; in: Neuroimaging; pp. 1-7; 2016.

Zhang, Qiang et al.: "CBCT-based 3D MRA and angiographic image fusion and MRA image navigation for neuro interventions"; in: Medicine; vol. 95, No. 32; pp. 1-7; Doi 10.1097/MD.0000000000004358; 2016.

International Search Report and Written Opinion dated Jul. 25, 2019.

* cited by examiner

GENERATING A MEDICAL RESULT IMAGE

PRIORITY STATEMENT

This application is the national phase under 35 U.S.C. § 371 of PCT International Application No. PCT/CN2018/111674 which has an International filing date of Oct. 24, 2018, which designated the United States of America, the entire contents of which are hereby incorporated herein by reference.

FIELD

Embodiments of the present invention generally relate to generating a medical result image.

BACKGROUND

It is known to combine three-dimensional (3D, volume) image data sets, each acquired with stand-alone medical imaging modalities using 3D/3D-registration techniques. For example, a computed tomography (CT) 3D-image or a magnetic resonance tomography (MRT) 3D-image could be fused with or overlaid on an angiography/angiographic 3D-image. It is further known to overlay a desired volume data set on to a two-dimensional (2D) fluoroscopy/fluoroscopic image to provide intuitive intra-procedural guidance by displaying the overlay. The overlaid volume may be dynamically updated with geometrical changes of the angiographic system, e.g. a C-arm angiographic x-ray system, which is used to acquire the fluoroscopic image. Thus, diagnostic medical imaging data sets which may be acquired routinely and/or long before an interventional procedure can thus be utilized to provide additional anatomical information. Using 3D CT-angiography (CTA) or MRT-angiography (MRA) detailed vascular information may be provided during interventional procedures such as catheterization, stenting or coiling procedures. Repetitive intra-procedural 2D/3D angiography acquisitions can thus be reduced, advantageously reducing overall x-ray dose and/or contrast agent burden for the patient. Examples for these procedures are e.g. described in ZHANG, Qiang et al.: "CBCTbased 3D MRA and angiographic image fusion and MRA image navigation for neuro interventions"; in: Medicine; Vol. 95, No. 32; pp. 1-7; DOI 10.1097/MD.0000000000004358; 2016 or ZHANG, Qiang et al.: "Three-dimensional image fusion of CTA and angiography for real-time guidance during neuro interventional procedures"; in: Neuroimaging; pp. 1-7; 2016.

As regards neuro interventions comprising endovascular treatment of vascular disorders with involvement of brain, medulla, head and/or neck as well endovascular treatment of other peripheral vascular malformations, it is particularly advantageous to provide an overview of the vasculature of the entire region of interest. This overview may be provided by producing a CTA or MRA 3D roadmap and registering it with a 3D angiography (e.g. Siemens DynaCT large volume or DynaCT 360 technology enabling a portrait scan of a patient using a 30*40 $cm^2$ detector, which covers a field of view (FOV) from aortic arch to the cranial end). However, patient positions usually differ between CTA/MRA and angiography acquisitions, mainly due to cervical vertebra distortions. This hampers 3D/3D bone structure based global registration and generally introduces inaccuracies during 3D vessel roadmapping.

To correct for these roadmap inaccuracies it is known to use an additional, preferably, intra-procedural digital subtraction angiography (DSA) to adjust any deviations between CTA/MRA and real-time vessel positions. This involves considerable contrast agent administration, as DSA is ideally repeated for different anatomical regions.

Alternatively, it is known to acquire individual 3D angiographies for the thoracic-cervical and cranial region, thereby ensuring best registration accuracy for the current region of interest while maintaining an overview of the entire supra-aortic circulation from aortic arch to intracranial vessels. Of course, 3D/3D registration needs to be performed individually for each 3D angiography acquisition (cf. ZHANG, Qiang et al.: "Three-dimensional image fusion of CTA and angiography for real-time guidance during neuro interventional procedures"; in: Neuroimaging; pp. 1-7; 2016).

SUMMARY

The inventors have discovered that both these approaches either involve additional contrast agent and/or X-ray dose burden for the patient.

At least one embodiment of the present invention provides alternative devices and/or methods which allow intra-procedural medical image overlay while keeping patient X-ray dose and contrast agent administration as low as possible.

Embodiments are directed to a method for generating a medical result image using a current image, a target image and a reference image; corresponding computing unit; medical imaging apparatus; computer-program product and computer-readable storage medium. Alternative and/or preferred embodiments are object of the claims.

In the following, a technical solution according to an embodiment of the present invention is described with respect to the claimed apparatuses as well as with respect to the claimed methods. Features, advantages or alternative embodiments described herein can likewise be assigned to other claimed objects and vice versa. In other words, claims addressing the inventive method can be improved by features described or claimed with respect to the apparatuses. In this case, e.g. functional features of the method are embodied by objective units of the apparatus.

A first embodiment of the present invention is directed to a method for generating a medical result image using a current image, a target image and a reference image. All images involved depict at least partially the same body region of a patient. The method includes defining at least one image segment within the target image, registering the reference image with the target image by establishing a registration matrix for each image segment within the target image, wherein the registration matrix is specific for the respective image segment, detecting a position of a surgical instrument in the current image, the position corresponding to an image segment of the target image, and generating the medical result image by fusing the current image and the reference image using the registration matrix assigned to the image segment according to the position of the surgical instrument within the current image.

Another embodiment of the present invention is directed to a computing unit for generating a medical result image using a current image, a target image and a reference image, all images depicting at least partially the same body region of a patient, comprising:

a definition unit adapted to define at least one image segment within the target image, a registration unit adapted to register the reference image with the target image by establishing at least one registration matrix for each image segment, a detection unit adapted to detect a position of a surgical instrument in the current image, the position corresponding to one image segment of the target image, and a generation unit adapted to generate the medical result image by fusing the current image and the reference image using the registration matrix assigned to the image segment according to the position of the surgical instrument.

Another embodiment of the present invention is directed to a medical imaging apparatus for generating a medical result image using a current image, a target image and a reference image, comprising a computing unit of an embodiment.

Another embodiment of the present invention is directed to a computer program product comprising program elements which induce a computing unit to perform the steps of the method according to an embodiment, when the program elements are loaded into a memory of the computing unit.

Another embodiment of the present invention is directed to a computer-readable medium on which program elements are stored that are readable and executable by a computing unit, in order to perform steps of the method according to an embodiment, when the program elements are executed by the computing unit.

BRIEF DESCRIPTION OF THE DRAWINGS

Characteristics, features and advantages of the above described embodiments of the invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general the figures are not to scale. In the following.

DETAILED DESCRIPTION OF THE EXAMPLE EMBODIMENTS

Figure 1:
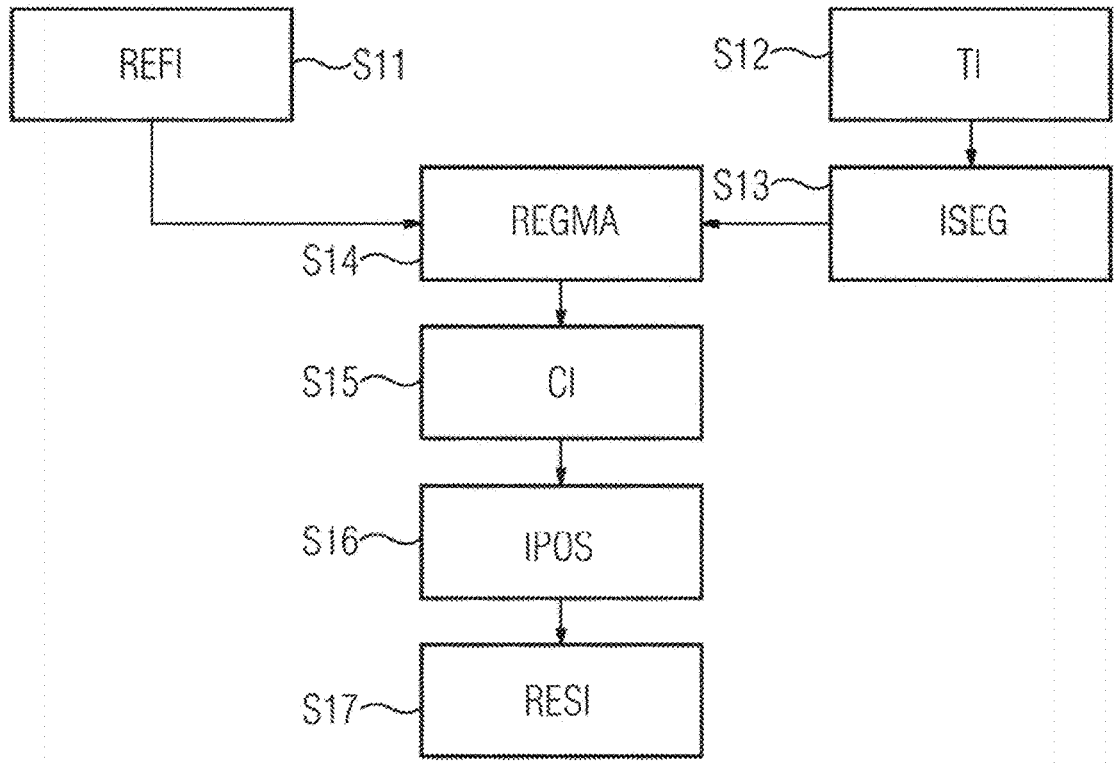
FIG. 1 shows a schematic flow chart of the inventive method according to an embodiment of the present invention.

A first embodiment of the present invention is directed to a method for generating a medical result image using a current image, a target image and a reference image. All images involved depict at least partially the same body region of a patient. The current image, the reference and the target image are all medical images which are acquired using a medical imaging apparatus, like a computed tomography system, magnetic resonance tomography system, a C-arm x-ray system or the like. The depicted body region of a patient corresponds to a body part, a body (sub-) area, like abdomen, thorax, neck, head and/or the like. The reference image, the target image and the current image depict at least in parts the same body region, i.e. they all comprise or show at least one common anatomical structure, organ, tissue or the like. Each of the reference image, the target image and the current image may comprise additional or extra anatomical structures which are not present in one of the other images. With other words, the current image, the target image and the reference image may cover different or the same field of view. Preferably, the reference image and the target image cover a bigger field of view than the current image.

While the target image preferably is a three-dimensional image, most preferably an angiography image, the current image is preferably a two-dimensional image, most preferably a fluoroscopy image. The current image preferably depicts a scene and/or a body part where a medical, i.e. a surgical intervention takes place.

Preferably, the target image and current image are acquired using the same medical imaging apparatus. Preferably they are acquired using a C-arm x-ray apparatus. Preferably, the target image and the current image are acquired in the course of a medical or surgical intervention on the patient, e.g. a catheterization, stenting or coiling procedure. Further preferably, the target image is acquired at the beginning of the medical intervention corresponding to an initial image of the imaged body region. Preferably, the current image is acquired at an arbitrary later point in time during the medical intervention.

Preferably, the reference image is a pre-procedural three-dimensional image, e.g. a magnetic resonance angiography image or a computed tomography angiography image. Most preferably, the reference image depicts an overview of vasculature of the images patient. With other words, the reference image is not acquired in the course of the same medical procedure, but preferably prior to the intervention. Further preferably, the reference image was acquired as a diagnostic image as part of a medical examination path and/or therapy path of a patient and is present in an electronic patient health record file and stored in a database e.g. in a local PACS (Picture Archiving and Communication System) of a medical enterprise or hospital or in a cloud data storage.

All images involved in an embodimnt of the inventive method may preferably be digital image files according to DICOM standard or the like. The images may all be loaded and processed by a computing unit according to an embodimnt of the present invention which will be described further below. Image processing, image manipulation and/or image analysis according to the invention take place in image space.

An embodimnt of the method comprises numerous steps.

A first step is directed to defining at least one image segment within the target image. The inventive method identifies at least one, preferably more than one image segments. With other words, the target image is subdivided into segments. A segment may be smaller in size than or of the same size as the target image. The segment position and/or size is preferably chosen, oriented and/or aligned with respect to patient anatomy depicted in the target image.

According to a preferred embodiment of the present invention the at least one image segment is defined by setting at least one separation plane which is oriented based on an anatomical structure in the depicted body region. Most preferably, the separation plane is set perpendicularly to a longitudinal body axis of the patient. By defining more than one separation planes several image segments can be defined corresponding to transversally oriented image segments.

According to another preferred embodiment of the present invention the separation plane is manually set by a user.

Thus, by visually analyzing the target image and displayed anatomical structures the user may individually position at least one separation plane which then serves as an image segment boundary. The separation plane may be aligned with at least one anatomical structure, e.g. a bony structure and/or an organ and/or specific landmarks present in the target image. Alternatively, the at least one separation plane may be set automatically by the inventive computation unit based on target image segmentation results and/or landmark and/or structure and/or texture detection results. Furthermore, a segmentation plane may be set semi-automatically by automatically suggesting a separation plane wherein the suggestion may be accepted and/or corrected by the user.

A second step of an embodiment is directed to registering the reference image with the target image by establishing a registration matrix for each image segment within the target image, wherein the registration matrix is specific for the respective image segment. Image registration in general describes the alignment of two images wherein differences in the images which may be caused e.g. by differences in view angle, using different medical imaging apparatuses, patient movement, anatomical changes over time, etc. With other words, both the reference and the target image are aligned to each other to compensate for addressed differences. A registration matrix corresponds to a sum of mathematical and/or geometrical and/or special transformations which when applied e.g. to the reference image space, optimally aligns the anatomical structures of the reference image with the corresponding structures of the target image. Likewise, target image can be aligned to the reference image. However, since target image and also the current image typically represent a more up to date anatomical state or condition of the patient, the reference image is preferably aligned to the target image. Preferably, prior to registering the reference image and the target image, anatomical structures/objects/organs/tissues/structures in both the images are segmented using segmentation techniques well known as such in the field of medical image processing. Furthermore, a pre-registration of the reference image to the coordinate system of the medical imaging apparatus used to acquire the target image may be necessary for registration.

According to a preferred embodiment of the present invention the registration of the reference image and the target image is performed using an intensity based, rigid transformation technique. Rigid registration is generally limited to linear transformations like rotation, translation, scaling or the like. Linear transformations are characterized in that they can only be applied globally to an image which means that local deviation differences between reference image and target image can only partially be accounted for. With other words, a rigid registration matrix is to be understood as a compromise or tradeoff of transformations which overall result in an alignment of anatomical structures which is however less than 100 percent alignment. An intensity based registration generally compares intensity patterns identified in the reference image and the target image to correspond to each other and tries to find transformations which cause an alignment of anatomical structures of reference image and target image. If considered necessary, a registration matrix established automatically according to the present invention may be manually corrected and/or adapted by a user.

According to the inventive concept of at least one embodiment, not only one registration matrix is established in this step, but at least two registration matrices are established. The registration matrices are specific for the corresponding image segments of the target image. With other words, the registration matrices are body region specific.

According to another preferred embodiment of the present invention, an image segment specific registration matrix is established based only on anatomical features located in the respective image segment. With other words, the registration procedure only considers anatomical features and or structures, e.g. organs, tissues, lesions, etc., which are located within the respective image segment. Thereby, the image segment specific registration matrix is more exact for the anatomical structures, preferably the bony structures, located within this segment than a registration matrix which was established considering the whole target image. Thus, at least two registration matrices are constructed which only account for anatomical structures in the respective image segment. Anatomical structures outside of the respective image segment are not considered for establishing the registration matrix for this segment. Therefore, the at least two registration matrices for different image segments may differ from each other. Each registration matrix thus represents transformation operations adapted to patient anatomy within the respective segment only.

A third step of an embodiment is directed to detecting a position of a surgical instrument in the current image, the position corresponding to an image segment of the target image. Here, an object detection procedures may be applied which is well known as such in the field of medical image processing. The surgical instrument my e.g. be a catheter, a stent or the like or only a specific part of an instrument.

According to a preferred embodiment of the present invention this step is performed using a two-dimensional real time instrument tracking technique. For example, an object detection procedure is described in LESSARD, S. et. al.: "Automatic detection of selective arterial devices for advanced visualization during abdominal aortic aneurysm endovascular repair", in: Med Eng Phys., 2015, Vol. 37(10), pp. 979-986, the entire contents of which are hereby incorporated herein by reference. Alternatively, a user may provide information on where a surgical instrument is located in the current image by providing manual input via a user interface.

This step is based on the inventive insight that the at least one image segment identified in the target image as well as the anatomical structures within this segment are also present in the current image. With other words the current position of the detected surgical instrument is assigned to one image segment by verifying which image segment of the target image the detected position belongs to. The detected position thus corresponds to one image segment as defined in the target image. With other words, Target image boundaries need to be transferred to the current image first, e.g. by using registration techniques for registering target image and current image. For example, target image and current image may be registered to a common coordinate system, preferably the coordinate system of the C-arm X-ray apparatus, to simplify this method step.

A fourth step of an embodiment of the inventive method is directed to generating the medical result image by fusing the current image and the reference image using the registration matrix assigned to the image segment according to the position of the surgical instrument within the current image. For fusing the current and the reference image, the registration matrix corresponding to the image segment the current surgical instrument position belongs to is first applied to the reference image to align anatomical structures to the target image and thus the current image, too. Then, reference image and current image are merged/fused/overlaid.

According to another preferred embodiment, the image segment specific registration matrix is applied globally to the reference image. Although the transformations defined in the segment specific registration matrix are based on anatomical structures within the respective image segment, this registration matrix is applied to the full reference image, not only the reference image sector corresponding to the image segment in the target image. Thus, highest registration accuracy for this image segment (comprising the instrument position) is provided in the result image accepting less overlay accuracy for the remaining image parts of the result image. The result image corresponds to an image overlay comprising information as regards an up-to-date position of the surgical instrument as well as a preferably global overview of vasculature and serves for intra-procedural guidance of a user.

At least one embodiment of this inventive method provides for intra-interventional or intra-procedural high registration accuracy for surgical image guidance by determining current instrument position and applying the registration matrix most accurate for the image segment corresponding to the detected instrument position.

According to a preferred embodiment of the present invention the current image is used as the target image in the method steps of defining at least one image segment within the target image and registering the reference image with the target image by establishing a registration matrix for each image segment within the target image, wherein the registration matrix is specific for the respective image segment. According to this embodiment the present invention advantageously requires only two images to generate the result image.

According to another preferred embodiment of the present invention the current image is repeatedly updated in the course of surgical intervention and the steps of detecting the instrument position and generating a result image are likewise repeated using the updated current image. With other words, the inventive method may be applied repeatedly in the course of medical intervention or surgery to repeatedly provide updated result images for interventional guidance. In each iteration or for each current image it is checked which image segment the current instrument position is located in. If instrument position moves from one image segment to another image segment between acquisitions of two consecutive current images, the registration matrix is updated, accordingly, for generating the result image for the second of the two consecutive current images. For all further iterations the updated registration matrix is used as long as the instrument tip stays within the respective image segment. In this embodiment the result image corresponds to an image overlay comprising information as regards a most current position of the surgical instrument during intervention as well as a preferably global overview of vasculature, wherein the registration matrix applied to the reference image is chosen in dependency of the surgical instrument position.

According to another preferred embodiment of the present invention the current image acquired first during surgical intervention is used as the target image in steps of defining at least one image segment within the target image and registering the reference image with the target image by establishing a registration matrix for each image segment within the target image. With other words, the target image corresponds to the first of numerous current images acquired during surgical intervention. By this the application or transfer of the at least one image segment defined using the target image to the numerous current images is advantageously simplified as current and images are acquired with the same medical imaging apparatus and thus being registered to the same coordinate system from the beginning.

According to another preferred embodiment of the present invention in the course of surgical intervention the steps of defining at least one image segment within the target image and registering the reference image with the target image by establishing a registration matrix for each image segment within the target image are repeated, wherein an updated current image is used as the target image. Thus at least one updated registration matrix is established, wherein the at least one updated registration matrix is applied in the step of generating the medical result image. This embodiment of the present invention advantageously accounts for severe changes between target image and current image which may occur during surgical intervention and which forbid to continue using the original target image and corresponding registration matrices for a current image.

Furthermore, according to this embodiment of the invention, the image segment specific registration matrix is applied globally to the reference image for generating the result image. With other words, the geometric transformations corresponding to a segment specific registration are not only applied segment-wise to the reference image, but to the full reference image. This approach acknowledges the fact that inaccuracies and/or deviations of the overlay of anatomical structures in the result image outside the image segment the surgical instrument is currently located in are not severely impacting the quality of interventional guidance, as long as the registration quality within this image segment is at maximum to provide optimal guidance where the surgical instrument is currently located.

According to another preferred embodiment of the present invention the steps of detecting the instrument position and generating a result image are performed in real time or near real time. This embodiment advantageously allows for instantaneous display of the result image and/or a consecutive series of updated result images for a user.

Another embodiment of the present invention is directed to a computing unit for generating a medical result image using a current image, a target image and a reference image. The computing unit comprises a definition unit adapted to define at least one image segment within the target image. The computing unit comprises a registration unit adapted to register the reference image with the target image by establishing at least one registration matrix for each image segment. The computing unit comprises a detection unit adapted to detect a position of a surgical instrument in the current image, the position corresponding to one image segment of the target image and the computing unit comprises a generation unit adapted to generate the medical result image by fusing the current image and the reference image using the registration matrix assigned to the image segment according to the position of the surgical instrument. The computation unit may optionally comprise an acquisition unit adapted to acquire and/or receive and/or load the current image, the target image and the reference image, e.g. from medical imaging apparatus, a PACS, a cloud storage or the like.

The computing unit according to an embodiment of the present invention is adapted to implement the inventive method. The computing unit may be configured to particularly carry out the step of generating the medical result image by fusing the current image and the reference image using the registration matrix assigned to the image segment according to the position of the surgical instrument. The computing unit may likewise be arranged to carry out all the steps of the inventive method for an individual medical imaging apparatus and/or for several medical imaging apparatuses in a hospital, a medical site or the like.

The computing unit can be realized as a data processing system or as a part of a data processing system. Such a data processing system can, for example, comprise a cloud-computing system, a computer network, a computer, a tablet computer, a smartphone or the like. The computing unit can comprise hardware and/or software. The hardware can be, for example, a processor system, a memory system and combinations thereof. The hardware can be configurable by the software and/or be operable by the software. Generally, all units, sub-units or modules may be at least temporarily be in data exchange with each other, e.g. via network connection or respective interfaces.

Another embodiment of the present invention is directed to a medical imaging apparatus for generating a medical result image using a current image, a target image and a reference image. The medical imaging apparatus comprises an embodiment of an inventive computing unit. Preferably, the computing unit is physically integrated into the medical imaging apparatus. Alternatively, the computing unit can be located physically separated from the medical imaging apparatus. A medical imaging apparatus is an imaging apparatus for medical purposes. A medical imaging apparatus in particular may relate to imaging using optical electromagnetic radiation and/or X-Ray radiation. In particular, a medical imaging apparatus may be a magnetic resonance imaging apparatus, a computed tomography imaging apparatus, an X-ray imaging apparatus, a positron emission tomography (PET) imaging apparatus and/or an ultrasound imaging apparatus. Most preferably, the medical imaging apparatus is a C-arm x-ray apparatus typically used for acquiring angiography and/or fluoroscopy images.

Another embodiment of the present invention is directed to a computer program product comprising program elements which induce a computing unit to perform the steps of an embodiment of the inventive method, when the program elements are loaded into a memory of the computing unit.

Another embodiment of the present invention is directed to a computer-readable medium on which program elements are stored that are readable and/or executable by a computing unit, in order to perform technical operations, e.g. comprising the steps of an embodiment of the inventive method, when the program elements are executed by the computing unit.

The realization of at least one embodiment of the invention by a computer program product and/or a computer-readable medium has the advantage that already existing providing systems can be easily adopted by software updates in order to work as proposed by an embodiment of the invention.

The computer program product can be, for example, a computer program or comprise another element next to the computer program as such. This other element can be hardware, for example a memory device, on which the computer program is stored, a hardware key for using the computer program and the like, and/or software, for example a documentation or a software key for using the computer program. The computer program product may further comprise development material, a runtime system and/or databases or libraries. The computer program product may be distributed among several computer instances.

FIG. 1 shows a schematic flow chart of the inventive method according to an embodiment of the present invention. In a first step S11 a reference image REFI is acquired. This step comprises either image acquisition using a medical imaging apparatus and/or loading of the corresponding reference image data set from a local or central storage unit like PACS or cloud storage into a computing unit 7 for further processing. The reference image REFI preferably is a three-dimensional MRA or CTA, showing an overview of vasculature which a least covers the body region of the patient to be imaged. Preferably the three-dimensional reference image is acquired using a contrast agent, as those images are best suited for imaging vasculature. The reference image REFI also depicts bony structures of the patient. In a second step S12 a target image TI is acquired. This preferably comprises image acquisition using a medical imaging apparatus, but may also comprise loading of the corresponding target image data set from a local or central storage unit like PACS or cloud storage into a computing unit for further processing. Target image TI preferably is a three-dimensional angiography, which is acquired using a C-arm x-ray imaging apparatus 1 under application of contrast agent at the beginning of a surgical intervention. Thus, also the target image TI depicts the vasculature of the patient.

The target image TI preferably has the same or similar field of view as reference image REFI, however may also have a smaller field of view. Also the target image TI depicts bony structures. While the target image TI corresponds to an intra-interventional image data set, the reference image REFI rather corresponds to an image acquired prior to or long before the surgical intervention. Thus, target image TI represents a current or up-to date state of patient anatomy in the imaged body region. In a third step S13 at least one image segment ISEG is defined in the target image TI.

Alternatively, the image segment ISEG may be defined in the reference image REFI. The image segment ISEG is aligned to and/or oriented according to anatomical structures, e.g. bones and/or bony landmarks. The image segment ISEG is defined e.g. by setting at least one separation plane SP which is aligned to and/or oriented according to anatomical structures in the depicted body region. Preferably, the target image TI is presented to a user via an output unit 48 and a separation plane SP is manually input via an input unit 50 by the user considering the depicted patient anatomy. For example, the user may draw a line at a desired position using an activated mouse cursor. For further user support, both the target image TI as well as the reference image REFI may be presented to the user. Based on local deviation between patient anatomy in both the images the user may individually decide on the number and position of image segments ISEG suitable for this patient. For example, three image segments ISEG may be defined.

Alternatively, the at least one separation plane SP may be set automatically by the computing unit 7 and presented to the user for confirmation or correction via input/output unit 48/50. Furthermore, step S13 may be carried out fully automatically without user input. Here, a segmentation of target image TI and/or reference image REFI to identify anatomical structures may be necessary first. Based on the segmented and analyzed anatomy like bones, organs, tissues and the like, segmentation planes SP may be set automatically. In a fourth step S14 target image TI and reference image REFI are registered to each other.

This step S14 comprises establishing a registration matrix REGMA for each image segment ISEG. The registration matrix REGMA for each image segment ISEG is specific for the image segment ISEG as it only accounts for anatomical features within the image segment ISEG. A registration matrix corresponds to a sum of mathematical transformations which when applied to each image element of the reference image REFI, bring the anatomical structures within the respective image segment ISEG in accordance with the corresponding anatomical structures in the target image TI. The registration preferably is an intensity-based, rigid registration.

In a further step S15 a current image CI is acquired. The current image CI corresponds to a two-dimensional fluoroscopy image acquired in the course of the same surgical intervention the target image TI is acquired in. The current image CI typically depicts a smaller field of view than the target image TI. With other words, the field of view of the current image CI is collimated to a smaller area of interest within the imaged body region, e.g. where surgical intervention takes place. The current image CI typically is acquired without contrast agent involved. To further reduce the contrast agent burden for the patient a current image CI may serve as the target image TI in steps S12, S13 and S14. Most preferably, numerous current images CI are acquired in the course of the surgical intervention, each current image CI depicting an up-to-date state of the surgical procedure and/or anatomy.

In detail, the current image CI depicts a position of (a part of) a medical instrument IPOS, preferably a catheter tip in the depicted vasculature. In another step S16 the current instrument position IPOS is detected using well known instrument tracking techniques. Preferably, the instrument is tracked using a two-dimensional real-time instrument tracking technique. As target image TI and current image CI are acquired using the same C-arm x-ray imaging apparatus 1, the instrument position IPOS may be easily transferred to the target image TI and assigned to one of the at least one image segments ISEG, wherein each image segment is also assigned a specific registration matrix REGMA (cf. above). In a last step S17 the registration matrix REGMA assigned to the image segment ISEG the instrument is located in in the current image CI, is used to generate a result image RESI by first applying the mentioned registration matrix REGMA to the reference image REFI and then fusing the current image CI and the reference image REFI. It is to be mentioned that the registration matrix REGMA may be established specifically, i.e. exclusively for the patient anatomy within the respective image segment ISEG. However, in step S17 the registration matrix REGMA is applied globally, i.e. to all image elements, i.e. voxels, of the reference image REFI.

Thus, the superposition or overlay of current image CI and transformed reference image REFI i.e. the result image RESI provides for optimal interventional guidance for the user in the depicted image area where the surgical instrument is located in. This is due to the fact that in the image segment ISEG comprising the instrument position IPOS the registration of the reference image REFI is conducted with the respective registration matrix REGMA specifically adapted to the patient anatomy in this image segment ISEG, wherein the registration matrix REGMA may be only suboptimally suited for the surrounding body areas. The result image RESI may be instantaneously presented to the user. Not only step S16, but also step S17 may be carried out in real time or near real time.

Figure 2:
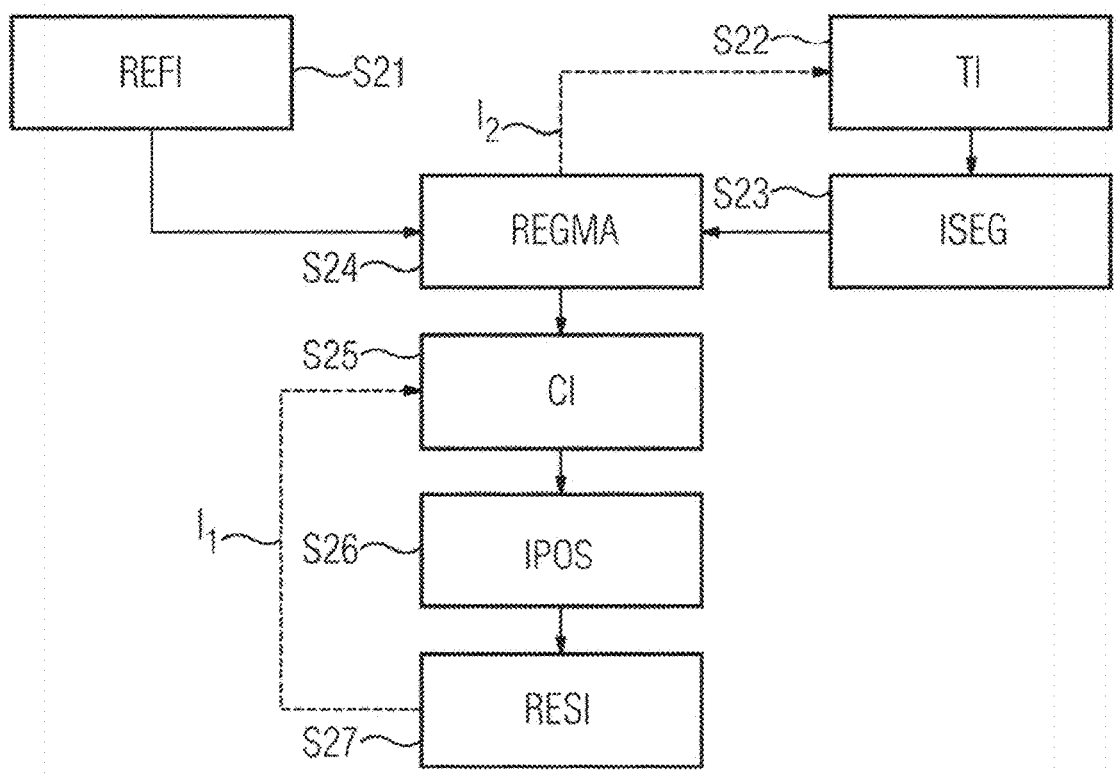
FIG. 2 shows a schematic flow chart of the inventive method according to another embodiment of the present invention.

FIG. 2 shows a schematic flow chart of the inventive method according to another embodiment of the present invention. Basically, steps S21, S22, S23, S24, S25, S26 and S27 correspond to the steps S11, S12, S13, S14, S15, S16 and S17, respectively, and may be carried out in the same manner as already described with respect to FIG. 1. However, FIG. 2 further comprises an iteration loop I1, which is based on an update of the current image CI during the surgical intervention. As already indicated with respect to FIG. 1, there may be several current images CI acquired during surgical intervention. Steps S25, the acquisition of a current image CI, step S26, the detection of a current position of the surgical instrument IPOS as well as step S27, the generation of the result image RESI using the registration matrix REGMA for the image segment ISEG the instrument is currently located in, are constantly repeated thus providing an updated result images RESI, each depicting the most recent position of the surgical instrument IPOS in the context of the global anatomical overview, especially vasculature overview as provided by the reference image REFI. According to step S15 in FIG. 1, the current image CI acquired first in the iteration loop I1 may be used as the target image TI.

Furthermore, FIG. 2 also comprises iteration loop I2, according to which the target image TI may likewise be updated in the course of surgical intervention to provide for at least one updated registration matrix REGMA according to step S24 for each image segment ISEG, in case anatomical deviations between current image CI or target image TI and reference image REFI are above a predefined threshold accepted at maximum for useful image registration. The target image TI may here be updated using a current image CI acquired in the course of the surgical intervention.

In the following, an embodiment of the present invention is again summarized describing a use case for neuro-intervention procedure. However, it is noted that an embodiment of the present invention is not limited to this special use case, but may be applied to other surgical intervention procedures as well as different body regions (e.g. abdomen or legs).

An embodiment of the present invention may e.g. advantageously be applied in surgical interventions like neuro interventions in the head, neck or spinal cord. Here, a three-dimensional diagnostic CTA/MRA reference image dataset REFI may fail for providing sufficient guidance during surgical intervention. This may mainly be due to cervical vertebra distortions, i.e. local anatomical deviations, which can hardly be accounted for using global registration techniques.

To overcome this hurdle, an embodiment of the present invention decomposes the global registration problem into a number of local registrations, such as e.g. a thoracic region (thoracic image segment) registration, cervical region (neck image segment) registration and cranial region (head image segment) registration, depending on the current position of the surgical instrument IPOS, i.e. the catheter.

With other words, an embodiment of the present invention performs automatic and region specific 3D/3D registration on basis of intensity based rigid transformation using the target image TI and the reference image REFI and combines it with 2D real time catheter tracking methods. As a result, higher registration accuracy is achieved in real time for a current C-arm position of a c-arm x-ray imaging apparatus and the current region of interest, i.e. the image segment ISEG the surgical instrument is currently located in, without additional contrast medium injection and/or angiography acquisition.

First, preferably two 3D volume data sets covering similar regions (e.g. pre-interventional CTA depicting vessel trees=reference image REFI and an intra-interventional low dose 3D non-contrasted angiography of the same patient=target image TI) are acquired. Next, separation planes SP are defined in the target image TI to separate different anatomical segments/regions ISEG based on common bony structures depicted in both 3D images, for example: thoracic, cervical and cranial regions. This is preferably carried out by user interaction to define the planes SP.

Figure 4:
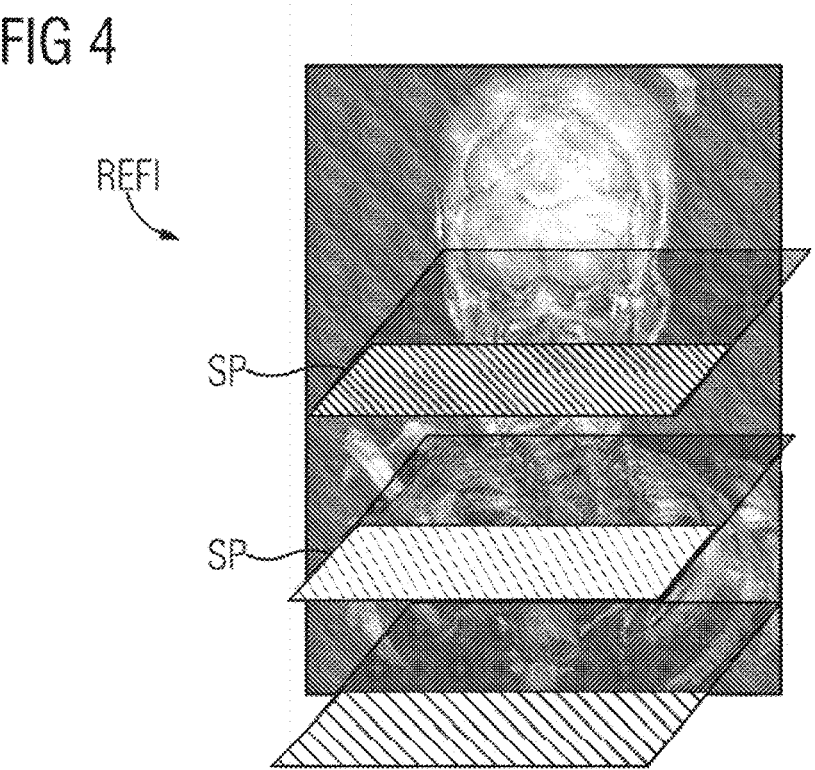
FIG. 4 shows a reference image comprising segmentation planes according to an embodiment of the present invention.

For example, the user could position the at least one separation planes aligned with the following landmarks: skull base, cervical vertebra, thoracic vertebra. FIG. 4 depicts a reference image REFI showing at least bony as well as vessel structures of the head, neck and thorax of a patient according to an embodiment of the present invention.

Figure 5:
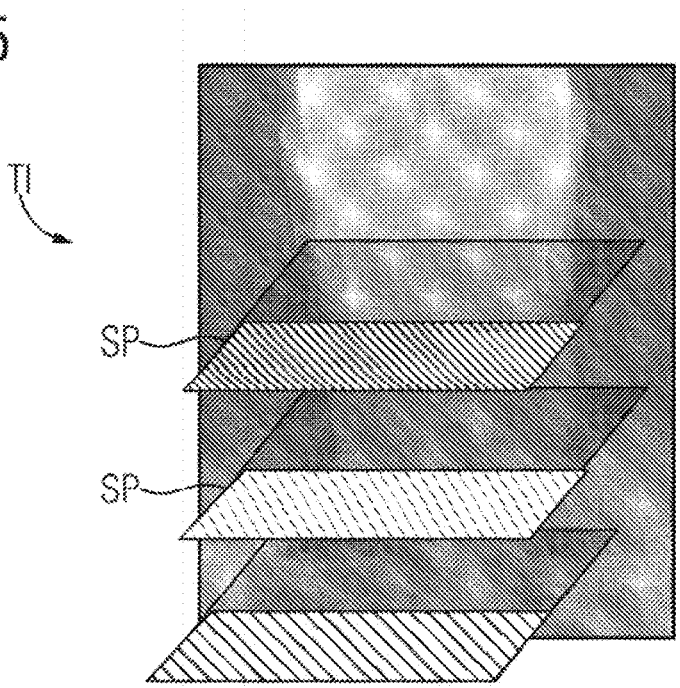
FIG. 5 shows a target image comprising segmentation planes according to another embodiment of the present invention.

FIG. 5 depicts a target image TI representing the same body region and likewise at least bony and vessel structures according to another embodiment of the present invention. Furthermore, in both the reference and the target images, REFI, TI, two separation planes SP are depicted, which serve to separate head image segment from neck image segment and further from thoracic image segment. Then, an intensity based automatic registration is performed for each corresponding anatomical image segment ISEG, which searches for rigid motion transformations including rotation, translation, scaling between the 3D CTA and 3D angiography.

The registration accuracy may be confirmed by the user wherein minor manual adjustment may be allowed. The registration matrices REGMA (here one for head, neck and thoracic image segment each) are saved separately. Each registration matrix REGMA will later be applied on the complete volume of the reference image REFI, i.e. each individual image element, but ensures highest registration accuracy only in its respective image segment ISEG.

Furtheron, intra-interventional two-dimensional fluoroscopy of the patient is started to generate at least one initial current image CI. Preferably, the 3D reference image REFI is registered to the current 3D axis of the C-arm x-ray angiographic apparatus using the registration matrix REGMA established for the thoracic image segment (as in the following catheter motion takes place from thorax to head), and is then overlaid onto the initial current image CI and displayed for initial interventional guidance. For example, the reference image REFI is virtually projected onto the 2D detector plane (comprising the initial current image CI) for the current geometry of the C-arm x-ray angiographic system 1. Also representations of the separation planes SP may be projected onto the current image CI. The 3D reference image REFI can thus and must further on in the procedure be dynamically updated with geometrical changes of the angiography system 1.

Using optical guidance provided by the virtual projection, catheterization may be started and continuous movement of e.g. the catheter tip position IPOS is traced using continuously acquired current images CI. Regarding the tracking, plenty of methods have been reported in literature, e.g. BAERT, S. A. M. et al.: "Guide wire tracking during endovascular interventions"; in IEEE Trans. Med. Imaging; Vol. 28, No. 8; pp. 965-972; 2003, or WANG, Peng et al.: "Robust Guidewire Tracking in Fluoroscopy"; in: Proc. IEEE Comput. Vis. Pattern Recognit; pp. 691-698; 2009, the entire contents of all of which are hereby incorporated herein by reference.

The catheter tip position IPOS as well as moving direction is continuously detected and recorded. Once the instrument position IPOS reaches or crosses the separation plane SP between thorax and neck, the registration is updated in the sense that registration matrix REGMA for the neck image segment is activated and used to update the 3D reference image REFI and generate a result image RESI by overlaying the transformed reference image REFI with the current image CI. The registration matrix REGMA for the neck image segment is applied as long as the catheter tip position IPOS is located within the neck image segment. As soon as the catheter tip moves beyond a separation plane SP again, registration is once again updated.

An embodiment of the present invention improves the accuracy of registration of each current image CI for the specific region of interest the surgical instrument is currently located in, and thus enhances the efficacy of 3D guidance during interventional procedures. No additional contrast medium injection or X-ray exposure is required, which improves clinical workflow and reduces iodinated contrast agent and radiation induced side effects for the patient.

Figure 3:
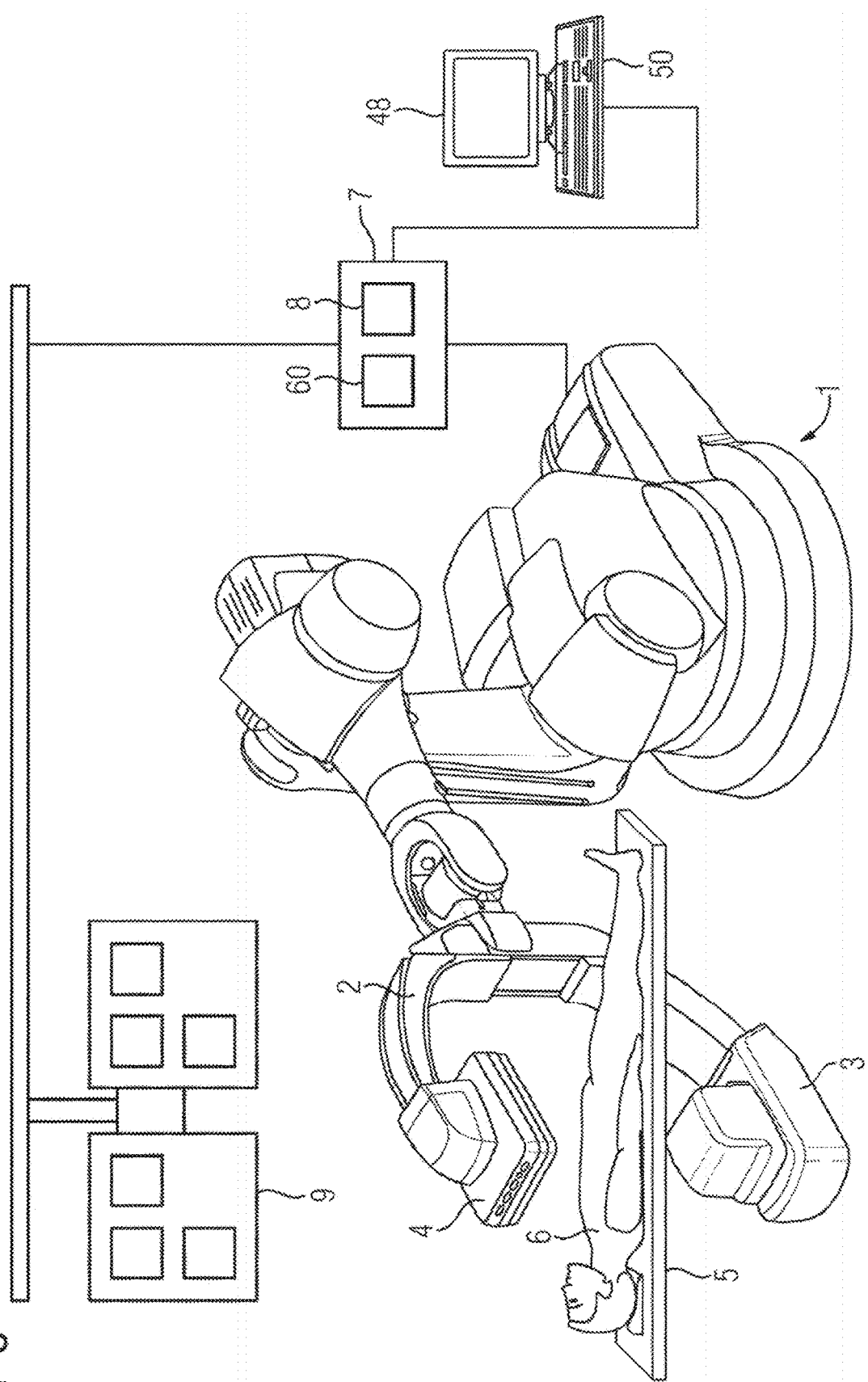
FIG. 3 depicts a schematic view of a medical imaging apparatus in form of a C-arm x-ray imaging apparatus comprising a computing unit according to an embodiment of the present invention.

FIG. 3 depicts a medical imaging apparatus 1 according to an embodiment of the present invention. The medical imaging apparatus is a monoplane angiographic x-ray system 1 in the form of a C-arm x-ray apparatus. The C-arm apparatus 1 comprises a stand formed as an articulated robot comprising six axis and arranged to hold the C-arm 2. The C-arm 2 comprises at its ends, respectively, an x-ray source 3, e.g. an x-ray tube unit and a collimator as well as an x-ray detector 4. The angiographic system 1 is rotatably mounted, it can be rotated around centers of rotation and/or axis of rotation which are arranged in and/or cross the plane of the C-arm 2. The angiographic system 1 as such may be installed in a fixed or movable manner. A patient bench 5 is located in the beam path of the x-ray source 3 to lair a patient 6 to be imaged with the C-arm 1.

The medical imaging apparatus 1 according to this embodiment comprises a computing unit 7 formed as a computer. The computing unit 7 may be physically part of the C-arm apparatus 1. The computing unit 7 is generally configured to receive and process the image signals detected by the x-ray detector 4, e.g. a current image CI and/or a target image TI. However, the computing unit 7 is likewise configured to receive and/or load medical images from internal or external storage units, e.g. the storage unit 60 or a cloud storage. Processed and or generated images, e.g. a current image CI and/or a result image RI may be displayed on a display screen of a monitor unit 9 to be considered by a user. Monitor unit may comprise several screen monitors, particularly flat screens. The computing unit 7 may alternatively be configured as independent unit not physically connected to the C-arm imaging system 1.

The computing unit 7 may further be connected with an output unit 48 and an input unit 50 for data exchange. Output unit 48 and monitor unit 9 may be realized as only one unit as well. The output unit 48 may e.g. serve for graphical display of a target image TI enable manual setting of separation planes and/or of separation planes within the target image TI automatically set and/or registration matrices automatically generated which may then be confirmed or corrected by a user using the input unit 50. Input unit 50 thus serves to select/confirm and/or correct information presented via the output unit 48. Output unit 48 may be formed as LCD-, plasma- or OLED-screen, which may further be a touch screen, which then also serves as input unit 50. Input unit 50 may further be realized as keypad, mouse, microphone or camera, the latter ones to detect and process either acoustic or visual input signals provided by a user.

The computing unit 7 may be connected to the x-ray detector 4 and/or the x-ray tube 3 for data exchange, wherein the connection may be either wired or wireless.

The computing unit 7 comprises an image processing unit 8. Image processing unit 8 is further sub-divided into a definition unit 81, a registration unit 82, a detection unit 83 and a generation unit 84. Sub-units or modules 81, 82, 83, 84 of the image processing unit 8 are configured to analyze, manipulate, process or generate x-ray images particularly reference images REFI, target images TI, current images CI and/or result images RESI.

For example, the definition unit 81 may be configured to perform object, landmark and/or texture analysis or the like on a medical image and to correspondingly segment anatomical structures like organs or tissues, particularly bones and vasculature, in a medical image. The definition unit 81 is further configured to define at least one image segment ISEG, e.g. by defining at least one separation plane SP which is aligned to the segmented anatomy in the target image TI.

The detection unit 83 is configured to detect a surgical instrument in a current image CI. The detection unit 83 is particularly configured to follow a moving instrument position and/or a moving instrument part position IPOS, e.g. a catheter tip, in the course of a surgical intervention using a plurality of consecutive current images CI.

The registration unit 82 is configured to register not only a reference image REFI to a target image TI, but also, where applicable and necessary, a target image TI to a current image CI. The registration matrix is particularly configured to establish individual registration matrices for individual image segments ISEG defined in the target image TI, wherein the individual registration matrices REGMA are image segment specific in the sense that each registration matrix REGMA only accounts for anatomical structures located within the respective image segment ISEG.

The generation unit 84 is configured to generate a result image RESI by identifying the registration matrix REGMA related to an image segment ISEG a surgical instrument is located in and then fusing the reference image REFI and the current image CI applying the identified registration matrix REGMA.

The computing unit 7 also comprises a storage unit 60. The storage unit 60 serves to store information on defined position and/or orientation of segmentation planes SP, detected landmarks, organs, tissues, structures or the like and/or established registration matrices REGMA, each for later use in the course of an embodiment of the inventive method.

The computing unit 7 may act in combination with a computer-readable medium, particularly to carry out an embodiment of the inventive method using a computer program comprising program code. The computer program may be stored on the computer-readable medium. The computer-readable medium may particularly be a CD, DVD, Blu-Ray Disc, a memory stick or a hard drive. The computing unit 7 may be realized in form of hard- and/or software. For example, the computing unit 7 may be realized as FPGA (field programmable gate array") or comprise an arithmetically logic unit.

In this embodiment the storage unit 60 stores at least one computer program which carries out all steps of an embodiment of the inventive method when the computer program is executed on the computing unit 7. The computer program may comprise program code. The computer program may be realized on a separate computing system. For example, the medical imaging apparatus 1 may be configured such that the computing unit 7 loads the computer program via internet or intranet into its internal random access memory for executing the steps according to an embodiment of the inventive method.

Wherever applicable, individual embodiments, their individual aspects and/or features, may be combined or exchanged with one another without limiting or widening the scope of the described invention, whenever such a combination or exchange is meaningful and in the sense of this invention. Advantages which are described with respect to one embodiment of the present invention are, wherever applicable, also advantageous to other embodiments of the present invention.

The invention claimed is:

1. A method for generating a medical result image (RESI) using a current image (CI), a target image (TI) and a reference image (REFI), each of the RESI, CI, TI and REFI depicting, at least partially, a same body region of a patient, the method comprising:
   defining at least one image segment within the target image;
   registering the reference image with the target image by establishing a registration matrix for each respective image segment within the target image, the respective registration matrix being specific for the respective image segment;
   detecting a position of a surgical instrument in the current image, the position corresponding to an image segment of the target image; and
   generating the medical result image by fusing the current image and the reference image using the respective registration matrix assigned to the respective segment according to the position of the surgical instrument within the current image.

2. The method of claim 1, wherein in the defining and the registering, the current image is used as the target image.

3. The method of claim 2, wherein the detecting and the generating are performed in real time or near real time.

4. The method of claim 2, wherein the image segment is defined by setting at least one separation plane, oriented based on an anatomical structure in a depicted body region.

5. The method of claim 2, wherein a registration of the reference image and the target image is performed using an intensity based rigid transformation technique.

6. The method of claim 2, wherein the detecting is performed using a two-dimensional real time instrument tracking technique.

7. The method of claim 1, wherein in a course of surgical intervention, the current image is repeatedly updated to form an updated current image, and the detecting and the generating are repeated using the updated current image.

8. The method of claim 7, wherein the current image acquired first during surgical intervention is used as the target image in the defining and the registering.

9. The method of claim 7, wherein in the course of surgical intervention, the defining and the registering are repeated to establish at least one updated registration matrix using an updated current image as the target image, wherein the at least one updated registration matrix is used in the generating, to generate the medical result image.

10. The method of claim 1, wherein in the registering, the image segment specific registration matrix is
   established based only on anatomical features located in the respective image segment, and
   applied globally on the reference image.

11. The method of claim 1, wherein the detecting and the generating are performed in real time or near real time.

12. The method of claim 1, wherein the image segment is defined by setting at least one separation plane, oriented based on an anatomical structure in a depicted body region.

13. The method of claim 12, wherein the separation plane is manually set by a user.

14. The method of claim 1, wherein a registration of the reference image and the target image is performed using an intensity based rigid transformation technique.

15. The method of claim 1, wherein the detecting is performed using a two-dimensional real time instrument tracking technique.

16. A computing unit for generating a medical result image (RESI) using a current image (CI), a target image (TI) and a reference image (REFI), each of the RESI, CI, TI and REFI images depicting, at least partially, a same body region of a patient, comprising:
- a definition unit, adapted to define at least one image segment within the target image;
- a registration unit, adapted to register the reference image with the target image by establishing at least one respective registration matrix for each respective image segment;
- a detection unit, adapted to detect a position of a surgical instrument in the current image, the position corresponding to one image segment of the target image; and
- a generation unit, adapted to generate the medical result image by fusing the current image and the reference image using the respective registration matrix assigned to the one image segment according to the position of the surgical instrument.

17. A computing unit comprising at least one processor, configured to implement a method for generating a medical result image (RESI) using a current image (CI), a target image (TI) and a reference image (REFI), each of the RESI, CI, TI and REFI depicting, at least partially, a same body region of a patient, the method comprising:
- defining at least one image segment within the target image;
- registering the reference image with the target image by establishing a registration matrix for each respective image segment within the target image, the respective registration matrix being specific for the respective image segment;
- detecting a position of a surgical instrument in the current image, the position corresponding to an image segment of the target image; and
- generating the medical result image by fusing the current image and the reference image using the respective registration matrix assigned to the respective image segment according to the position of the surgical instrument within the current image.

18. A medical imaging apparatus for generating a medical result image using a current image, a target image and a reference image, comprising the computing unit of claim 16.

19. A non-transitory computer program product comprising program elements to induce at least one processor to perform the method of claim 1, when the program elements are loaded into memory of the at least one processor and executed by the at least one processor.

20. A non-transitory computer readable medium storing program elements, readable and executable by at least one processor, to perform the method of claim 1, when the program elements are executed by the at least one processor.

* * * * *